United States Patent [19]

Ooms et al.

[11] Patent Number: 5,478,961
[45] Date of Patent: Dec. 26, 1995

[54] PROCESS FOR PREPARTING ARYL CARBONATES

[75] Inventors: Pieter Ooms, Krefeld; Norbert Schön, Darmstadt; Hans-Josef Buysch, Krefeld, all of Germany

[73] Assignee: Bayer Aktiengesellschaft, Leverkusen, Germany

[21] Appl. No.: 272,797

[22] Filed: Jul. 11, 1994

[30]   Foreign Application Priority Data

Jul. 19, 1993 [DE]   Germany .......................... 43 24 153.0

[51] Int. Cl.[6] ................................................. C07C 69/96
[52] U.S. Cl. .......................... 558/270; 558/271; 558/273; 558/274
[58] Field of Search .................................. 558/170, 271, 558/273, 274

[56]   References Cited

U.S. PATENT DOCUMENTS

| | | | |
|---|---|---|---|
| 2,362,865 | 11/1994 | Tryon et al. | 260/463 |
| 5,167,946 | 12/1992 | Mullins et al. | 423/481 |
| 5,239,105 | 8/1993 | Pews et al. | 558/274 |

*Primary Examiner*—José G. Dees
*Assistant Examiner*—Dwayne C. Jones
*Attorney, Agent, or Firm*—Connolly & Hutz

[57]   ABSTRACT

Carbonates with aromatic ester groups may be prepared by reacting aromatic monohydroxy compounds with phosgene or with chloroformates of aromatic monohydroxy compounds, wherein the process is performed at a temperature in the range 50°–350° C. in the presence of aluminosilicates as heterogeneous catalysts.

4 Claims, No Drawings

PROCESS FOR PREPARTING ARYL CARBONATES

FIELD OF THE INVENTION

The present invention relates to a process for preparing carbonates with aromatic ester groups by reacting aromatic monohydroxy compounds with phosgene or chloroformates of aromatic monohydroxy compounds with the elimination of hydrogen chloride in the presence of aluminosilicates as heterogeneous catalysts.

BACKGROUND AND PRIOR ART

It is known that aryl carbonates may be obtained by phase interface phosgenation (Schotten-Baumann reaction) of aromatic hydroxy compounds. Here, the use of solvents and caustic soda solution is a disadvantage because partial saponification of phosgene or chloroformate may take place due to the presence of alkali. In all cases, the large amount of sodium chloride which is produced is linked with pollution of the waste water. Furthermore, care has to be taken to recover the solvent, wherein effective protection of the environment must be ensured.

Therefore a condensation process which does not use solvents, in the presence of tetramethylammonium halides as homogeneous catalysts, has been suggested (U.S. Pat. No. 2,837,555). Here, however, the amounts of catalyst required are relatively large. As a rule 5–7 percent by weight of catalyst, with reference to the amount of phenol used, must be used in order to obtain economic rates of reaction. Reaction temperatures of 180°–215° C. are associated with the risk of decomposition of the thermally labile tetramethylammonium halides. Furthermore, the catalyst must subsequently be removed by washing with water, which makes its recovery very difficult. In addition, far more than the stoichiometric amount of phosgene is consumed.

According to another process (U.S. Pat. No. 3,234,263), diphenyl carbonates are obtained by heating phenyl chloroformates in the presence of large amounts of alkali/alkaline earth metal compounds or tertiary nitrogen bases as catalysts. This process has the disadvantage, however, that elevated temperatures are required and the catalysts such as alkali/alkaline earth metal compounds must be partially dissolved in order to achieve only approximately economically acceptable reaction times. In this process half the phosgene initially introduced is lost in the form of $CO_2$. In addition, the chloroformate must be synthesized in a quite separate process step.

According to CA-A-2 058 359 (U.S. Pat. No. 5,167,946), diaryl carbonates are obtained by phosgenation of aromatic hydroxy compounds in the presence of aluminium compounds which are at least partially soluble under the reaction conditions or which are converted into soluble aluminium halides and obviously act as homogeneous catalysts in this form (cf. U.S. Pat. No. 2,362,865, col. 1, lines 45–53). This is why aluminium trichloride (solubility) is particularly preferred. Although very good yields are obtained, it is difficult to separate the catalysts from the products. In the case of distillation, account must be taken of the fact that these compounds have a certain volatility and that thermal decompositions may occur due to these aluminium compounds which lead to impurities, a reduction in quality and decreased yields. The same applies to the process in U.S. Pat. No. 2,362,865, which still mentions the use of titanium, iron, zinc and tin as metals or as their soluble salts, especially the chlorides and phenolates, as catalysts.

Thus, it appears sensible to use heterogeneous, insoluble catalysts which makes working up the reaction mixture a great deal easier. There have also been proposals relating to this. Thus, according to the disclosure in EP-A 516 355, aluminium trifluoride is particularly recommended, this being optionally applied to a carrier such as aluminosilicates. However, the synthesis of aluminium trifluoride involves With handling fluorine or hydrofluoric acid, which are very toxic compounds, and thus also complicated and expensive apparatus.

SUMMARY OF THE INVENTION

The object of the invention is thus to develop simpler, accessible, effective heterogeneous catalysts.

It has now been found that aluminosilicates are outstanding catalysts for the reaction of phosgene or chloroformates with aromatic hydroxy compounds. This is particularly surprising and unexpected because such compounds are known to be inert according to the data in EP-A 516 355. Catalytic activity in the sense of the present invention has not been reported. On the contrary, aluminosilicates are preferably mentioned as inert support materials.

Accordingly, the present invention provides a process for preparing aryl carbonates by reacting aromatic monohydroxy compounds with phosgene or chloroformates of aromatic monohydroxy compounds, which is characterised in that the process is performed at a temperature in the range 50°– 350° C., at a pressure of 0.2 to 20 bar in the presence of aluminosilicate as a heterogeneous catalyst.

DESCRIPTION OF THE PREFERRED EMBODIMENTS

The process according to the invention has the great advantage that the catalyst can be separated very easily and no impurities remain in the crude reaction product. Therefore working up is greatly simplified.

Aromatic monohydroxy compounds for the process according to the invention are those of the formula

$$Ar^1-OH \qquad (I),$$

in which $Ar^1$ represents phenyl, naphthyl, anthryl, phenanthryl, indanyl, tetrahydronaphthyl or the radical from a 5- or 6-membered aromatic heterocyclic compound with 1 or 2 hetero-atoms from the group comprising N, O and S, wherein these isocyclic or heterocyclic radicals may be substituted by 1 or 2 substituents such as straight-chain or branched $C_1$–$C_4$-alkyl groups, straight-chain or branched $C_1$–$C_4$-alkoxy groups, which may be substituted with phenyl, cyano and/or halogen (e.g. F, Cl, Br), and wherein, furthermore, the heterocyclic radicals may be linked with a fused benzene ring.

Examples of aromatic monohydroxy compounds of the formula (I) are:

phenol, o-, m- and p-cresol, o-, m- and p-isopropylphenol, the corresponding halogeno or alkoxyphenols, such as p-chlorophenol or p-methoxyphenol, also monohydroxy compounds of naphthalene, anthracene and phenanthrene, and 4-hydroxy-pyridine and hydroxyquinoline. Optionally substituted phenols are preferably used, quite particularly preferably phenol itself.

The process according to the invention may be performed with either phosgene or with chloroformates of aromatic monohydroxy compounds. In the event that phosgene is used, the chloroformate is produced initially and this then reacts with further aromatic monohydroxy compound present in the reaction mixture to give a diaryl carbonate.

If chloroformates and an aromatic monohydroxy compound are used initially, then symmetric or asymmetric carbonates may be obtained.

Accordingly, aromatic chloroformates which are suitable for the process according to the invention are those of the formula (II)

Ar—OCOCl        (II), in which Ar has the same meaning as that given for formula (I).

Aluminosilicates which are suitable as heterogeneous catalysts are zeolites, clays (layer silicates) and synthetic aluminosilicates which possess neither the zeolite nor the layer silicate structure.

Zeolites are crystalline, synthetic or naturally occurring aluminosilicates with an open 3-dimensional structure (see D. W. Breck in "Zeolite Molecular Sieves", Wiley Interscience, 1974, p. 133–180; Ullmanns Enzyklopädie der technischen Chemie, 4th edition, vol. 17, p. 9–18, Verlag Chemie, Weinheim, N.Y.).

Zeolites may be described by the general formula (III)

$M_{2/n}O-Al_2O_3-xSiO_2-yH_2O$        (III), in which

M represents cations such as protons or any cations of metals in Mendeleev's Periodic Table of the elements and n represents the valency of the cation, x represents the molar ratio $SiO_2/Al_2O_3$, wherein x may be a number from 1.0–50.0, preferably 2.0–25.0, and y represents a number from 0 to 9.

Metal cations which may be mentioned by way of example are: Na, K, Ca, Mg, lanthanides, Ti, Sn, Zn, Fe, Ni, Co, Cu, Nb, Ta, Zr, etc.

Zeolites which are suitable for the process according to the invention are zeolites with the A, X, Y (faujasite type) and L structure, zeolites of the pentasil type such as ZSM 5, 11, 22, 23, mordenite, offretite, phillipsite, sodalite, omega and materials which are similar to zeolites such as AlPOs and SAPOs, zeolites with structure A, of the faujasite type such as X, Y and also L, ZSM 5, ZSM 11, mordenite, offretite, omega, SAPO 5, 11 and 34 and AlPO 5 and 11 are especially suitable and zeolites with the structure A, X and Y and ZSM 5, mordenite, SAPO 5, 11 and 34 and AlPO 5 and 11 are quite particularly preferable. They may be used separately or as a mixture.

The clays to be used according to the invention are known, e.g. from Kirk-Othmer "Encyclopedia of Chemical Technology" 2nd ed. 1964, vol. 5, p. 541–561. In this entry they are classified as:

A) The kaolin type such as kaolinite, dickerite, nacrite (all $Al_2O_3$ —$SiO_2$ —$2H_2O$) or anauxite ($Al_2O_3$ —$3SiO_2$ —$2H_2O$) or halloysite ($Al_2O_3$ —$2SiO_2$ —$2H_2O$) or endellite ($Al_2O_3$ —$2SiO_2$ —$4H_2O$) and B) the spinel type produced by heating the kaolin types, C) serpentine types, in which 3 Mg ions have replaced 2 Al ions in the kaolin species, such as $(Mg_3Si_2O_5(OH)_4)$ and amesite $Mg_4Al_2Si_2Al_2O_{10}$ $(OH)_8$ and iron-containing minerals such as Cronstedite $(Fe_2^{2+}Fe^{3+})$ $(SiFe^{3+})O_5(OH)_4$ and chamosite $(Fe^{2+}, Mg)_{2.3}$ $(Fe^{3+}Al)_{0.7}(Si_{1.14}Al_{0.86})O_5(OH)_4$ and the nickel or cobalt species, some of which may be obtained synthetically, D) aluminosilicates of the montmorillonite type, such as e.g. montmorillonite $[Al_{1.67}Mg_{0.33}(Na_{0.33})]$ $Si_4O_{10}(OH)_2$ beidellite $Al_{2.17}[Al_{0.33}(Na_{0.33})Si_{3.17}]O_{10}(OH)_2$ nontronite $Fe^{3+}[Al_{0.33}(Na_{0.33})Si_{3.67}]O_{10}(OH)_2$ hectorite $Mg_{2.67}Li_{0.33}(Na_{0.33})Si_4O_{10}(OH,F)_2$ saponite $Mg_{1.48}$ $[Mg_{0.14}Al_{0.74}Fe^{3+}]$ $[Al_{0.99}Si_{3.01}]O_{10}(OH)_2X_{0.33}$ as well as types which contain $Cu^{2+}$, $Co^{2+}$ or $Ni^{2+}$(X= halogen) such as volkonskoite, medmontite or pimelite.

This type of clay may be used separately or as a mixture. Naturally occurring and synthetic clays may be used.

Clays described as the "montmorillonite" type are preferred and montmorillonite itself is particularly preferred.

The aluminosilicates may be used in their original form which contains water or be (partially) dried. They may also be acid activated. Acid activation is performed, for instance, by treatment with acids, preferably inorganic acids.

Any mixtures of the previously mentioned zeolites and/or clays may be used.

Synthetic aluminosilicates, which are neither zeolites nor layer silicates are, for example, "pillared clays", as described in Mat. Res. Soc. Synp. Proc., vol. 111, p. 257 ff. 1988, in Applied Clay Science, vol. 2, p. 309 ff. 1987 or NATO ASI Ser., ser. C. vol. 231, p. 271 ff. 1988, or products which are produced by the mutual precipitation of hydrolysable aluminium and silicon compounds in aqueous medium, optionally in the presence of inert carriers or dispersants, and subsequent calcination.

The catalysts may be used as a powder or moulded items and after reaction are separated by filtration, sedimentation or centrifuging. In the event that they are used in a fixed bed arrangement, the aluminosilicates are preferably used as moulded items such as spheres, cylinders, rods, hollow cylinders, rings, etc.

The aluminosilicate catalysts mentioned are used, when working with a suspended catalyst in a stirred vessel or bubble column, in amounts of 0.5 to 100 wt. %, preferably 5 to 100 wt. % and particularly preferably 5 to 50 wt. %, with reference to the amount of monohydroxy compound used.

In the case of a continuous method of working in a counter- or co-current or in the trickle phase on a fixed bed catalyst, catalyst loads of 0.1 to 20 g of aromatic hydroxy compound per g of catalyst per hour, preferably 0.2 to 10 $g.g^{-1}.h^{-1}$ and particularly preferably 0.2 to 5 $g.g^{-1}.h^{-1}$ are used.

Aluminosilicates used in batchwise tests may be used again without purification when the same feed material is used. If the feed material is changed, the aluminosilicates are conveniently purified by extraction with an inert solvent, such as are mentioned later for example as reaction media, or with alcohols such as methanol, ethanol, isopropanol or butanol, with esters or amides of acetic acid or by treatment with superheated steam or air.

When using a continuous method of working, the aluminosilicates used may remain in the reactor for a long time. Regeneration is generally not worthwhile. It may take place however, by the passage of superheated steam, optionally with the addition of small amounts of air (about 0.1 to 20 wt. %, with reference to the amount of steam used), at 150° to 800° C. or by the passage of dilution gases such as nitrogen, carbon monoxide or carbon dioxide which contain 0.01 to 5 wt. % of oxygen or by means of carbon dioxide on its own at 200° to 800° C. The regeneration temperature is preferably 250°–700° C., particularly preferably 250° to 600° C.

The process according to the invention is performed at a temperature in the range 50°–350° C., preferably 100°–300° C., particularly preferably 100°–250° C. The temperature may be changed within the range mentioned while performing the process according to the invention, in a preferred manner being raised.

The process according to the invention is performed at a pressure of 0.2–20 bar, preferably 1.0–5 bar.

The process according to the invention may be performed with the help of solvents such as aliphatic and aromatic hydrocarbons such as pentane, hexane, octane, benzene, xylenes, diethylbenzene, alkylnaphthalenes, biphenyl, halogenated hydrocarbons such as dichloromethane, trichloroethylene, etc.

The process is preferably performed in the melt by passing, for example, phosgene or a chloroformate of the formula (II) into a suspension of aluminosilicate in a melt of the aromatic monohydroxy compound of the formula (I) and separating the catalysts after completion of the reaction, e.g. by filtering or centrifuging.

A further preferred embodiment of the synthesis is by bubbling gaseous phosgene or phosgene/hydrogen chloride mixtures or gaseous chloroformates of the formula (II) into a melt of the aromatic monohydroxy compound of the formula (I), with aluminosilicate contact catalyst suspended therein, in a continuously operated bubble column or bubble column cascade.

A further preferred mode of operation is the co-current process in which the aromatic hydroxy compound of the formula (I) and phosgene or chloroformate of the formula (II) are applied in a co-current from the top onto a catalyst packing arranged in a tube and hydrogen chloride and phosgenated products are withdrawn below at the foot of the tube.

A further preferred embodiment with particularly favourable results comprises performing the reaction according to the invention in the trickle phase, wherein the aromatic monohydroxy compound of the formula (I) is introduced as the melt or in the form of a solution to the top of a bed of aluminosilicates and this liquid stream encounters a stream of phosgene or chloroformate of the formula (II) flowing up from below. This embodiment is expediently performed in a vertical tubular reactor which may also contain intermediate partitions for improved distribution of gas and liquid streams.

The molar ratio of the reaction partners is aromatic monoyydroxy compound of the formula (I) to phosgene of about 0.5–3:1, preferably 1.5–3:1. The equivalent molar ratio in this case is 2:1.

In a corresponding manner, the aromatic monohydroxy compound of the formula (I) reacts with a chloroformate of the formula (II) in the molar ratio of 0.25 to 4:1, preferably 0.8–1.5:1. In this case the equivalent molar ratio is 1:1.

The crude aromatic carbonate obtained by heterogeneous catalysis is frequently very pure and may even be used in this form for many purposes, after degassing residual hydrogen chloride or other volatile substances. For uses with more stringent demands, the carbonate may optionally be further purified, e.g. by distillation or crystallisation.

The aryl carbonates are suitable intermediates for preparing e.g. phenylurethanes, polycarbonates and active substances.

EXAMPLES

Example 1

In a planar-section pot with flow spoilers, blower/stirrer and reflux condenser, 0.75 mol/h of phosgene was bubbled through 141 g (1.50 mol) of phenol in the presence of 14.1 g (10 wt. % w.r.t. phenol) of powdered H-SAPO 5. After about 2 hours reaction at 140° C., the phenol conversion was 7.1%, wherein 4.9 g of phenyl chloroformate and 8.0 g of diphenyl carbonate were formed. The selectivity to give the carbonate and phenyl chloroformate was greater than 99%.

Example 2

Example 1 was repeated at 160° C. After 2 h reaction time, the phenol conversion was 11.9%, wherein 0.6 g of phenyl chloroformate and 18.6 g of diphenyl carbonate were formed. The selectivity to give the carbonate and phenyl chloroformate was greater than 99%.

Example 3

Example 1 was repeated using 14.1 g of powdered H-ZSM 5 at 160° C. After 2 h reaction time the phenol conversion was 8.3%, wherein 0.5 g of phenyl chloroformate and 12.4 g of diphenyl carbonate were formed. The selectivity to give the carbonate and phenyl chloroformate was ca. 96%.

Example 4

Example 1 was repeated using 14.1 g of powdered H-Y at 160° C. After 2 h reaction time the phenol conversion was 11.0%, wherein<0.1 g of phenyl chloroformate and 17.5 g of diphenyl carbonate were formed. The selectivity to give the carbonate was ca. 99%.

Example 5 (for comparison)

Example 1 was repeated without the addition of aluminosilicate. After 4 h at 160° C. the phenol conversion was<0.2%.

Example 6

In a 3-necked flask fitted with a thermometer and reflux condenser, a mixture of 9.4 g (0.1 mol) of phenol and 15.7 g (0.1 mol) of phenyl chloroformate was heated in the presence of 0.94 g (10 wt. % w.r.t. phenol) of powdered H-ZSM 5. After 2 h at 160° C. a phenol conversion of 72% to give diphenyl carbonate was found. The selectivity was> 99%.

Example 7

Example 6 was repeated, but using 0.94 g of powdered H-Y and 3 h at 120° C. Phenol conversion to give diphenyl carbonate was 55% and selectivity>99%.

Example 8

Example 6 was repeated, but using 0.94 g powdered H-Y and 1 h at 160° C. Phenol conversion to give diphenyl carbonate was 70% and the selectivity>99%.

Example 9

Example 6 was repeated, but using 0.94 g of powdered SAPO 11 and 2 h at 160° C. Phenol conversion to give diphenyl carbonate was 64% and selectivity>99%.

Example 10

Example 6 was repeated, but using 0.94 g of powdered ALPO 11 and 3 h at 160° C. Phenol conversion to give diphenyl carbonate was 91% and after 5 h 97%. Selectivity>99%.

Example 11

Example 6 was repeated, but using 0.94 g of powdered montmorillonite KSF/O (Südchemie) and 5 h at 160° C. Phenol conversion was 55% and the selectivity>99%.

Example 12

Example 6 was repeated, but using 0.94 g of powdered Na-X and 3 h at 160° C. Phenol conversion was 90% and selectivity> 99%.

Example 13

Example 6 was repeated, but using 0.94 g of powdered Na-A and 3 h at 160° C. Phenol conversion was 56% and selectivity> 99%.

We claim:

1. A process for preparing aryl carbonates by reacting aromatic monohydroxy compounds with phosgene or chloroformates of aromatic monohydroxy compounds, characterised in that the reaction is performed at a temperature in the range 50°–350° C. under a pressure of 0.2 to 20 bar in the presence of one or more aluminosilicate zeolites as heterogeneous catalysts.

2. A process according to claim 1, wherein the aluminosilicate is a zeolite of the formula $$M_{2/n} \cdot Al_2O_3 \cdot xSiO_2 \cdot yH_2O$$

in which

M represents a metal cation, n represents the valency of the cation, x represents the molar ratio $SiO_2/Al_2O_3$, wherein x may be a number from 1.0–50.0, and y is a number from 0–9.

3. The process according to claim 1, wherein the aluminosilicate is an ALPO zeolite.

4. The process according to claim 1, wherein the aluminosilicate is a SAPO zeolite.

* * * * *